(12) United States Patent
Postma et al.

(10) Patent No.: US 9,227,947 B2
(45) Date of Patent: Jan. 5, 2016

(54) PROCESS FOR THE MANUFACTURE OF EPICHLOROHYDRIN

(71) Applicant: Momentive Specialty Chemicals Inc., Columbus, OH (US)

(72) Inventors: Ron Postma, Vondelingenplaat (NL); Prasad Muppa, Vondelingenplaat (NL)

(73) Assignee: HEXION INC., Columbus, OH (US)

( * ) Notice: Subject to any disclaimer, the term of this patent is extended or adjusted under 35 U.S.C. 154(b) by 0 days.

(21) Appl. No.: 14/285,124

(22) Filed: May 22, 2014

(65) Prior Publication Data

US 2014/0256968 A1 Sep. 11, 2014

Related U.S. Application Data

(63) Continuation of application No. 13/056,835, filed as application No. PCT/EP2009/004976 on Jul. 9, 2009, now Pat. No. 8,802,873.

(30) Foreign Application Priority Data

Aug. 1, 2008 (EP) ..................................... 08075681

(51) Int. Cl.
*C07D 307/00* (2006.01)
*B01J 27/24* (2006.01)
*B01J 23/32* (2006.01)
*C07D 301/12* (2006.01)
*B01J 21/00* (2006.01)
*B01J 23/34* (2006.01)

(52) U.S. Cl.
CPC ............... *C07D 301/12* (2013.01); *B01J 21/00* (2013.01); *B01J 23/34* (2013.01)

(58) Field of Classification Search
CPC ........ C07D 3013/12; B01J 21/00; B01J 23/34
USPC .................................. 549/531; 502/200, 324
See application file for complete search history.

(56) References Cited

U.S. PATENT DOCUMENTS 4,859,795 A 8/1989 Gerdau et al.
6,610,864 B2 8/2003 Krebs et al.

FOREIGN PATENT DOCUMENTS

CN 1353102 6/2002
CN 101045717 6/2002
CN 1754866 4/2006

*Primary Examiner* — Andrew D Kosar
*Assistant Examiner* — Raymond Covington

(57) ABSTRACT

The invention relates to a process for the manufacture of epichlorohydrin ("ECH")
by catalytic oxidation of allyl chloride ("AC") with an oxidant wherein the catalytic oxidation is performed in an aqueous reaction medium, wherein a water-soluble manganese complex is used as oxidation catalyst,
followed by the isolation of epichlorohydrin.

17 Claims, No Drawings

PROCESS FOR THE MANUFACTURE OF EPICHLOROHYDRIN

RELATED APPLICATION DATA

This application is a continuation application of co-pending U.S. patent application Ser. No. 13/056,835, with a filing date of Jan. 31, 2011, which application claims the benefit of PCT Application PCT/EP2009/004976 with an International Filing Date of Jul. 9, 2009, published as WO 2010/012360, which PCT Application PCT/EP2009/004976 further claims priority to European Patent Application No. EP08075681.0 filed Aug. 1, 2008, the entire contents of all are hereby incorporated by reference.

TECHNICAL FIELD

The invention relates to a process for the manufacture of epichlorohydrin ("ECH") by catalytic oxidation of allyl chloride ("AC") using hydrogen peroxide and a manganese complex.

BACKGROUND ART

ECH (also known as "EPI") is of particular interest. It is for instance used as a building block in the manufacture of plastics, epoxy resins, phenoxy resins and other polymers. It has been used as a solvent for cellulose, resins and paints and it has found use as an insect fumigant. ECH may react with water, forming the corresponding diol.

Conventional ECH production routes involve the use of chloride containing oxidants, such as HOCl. This method suffers a.o. from a relatively large amount of co-produced chloride salts.

Despite the strong interest in ECH, a high atom-efficient production route without the coproduction of salts and/or other byproducts is not yet available. Moreover, alternative preparation methods suffer from side reactions and/or isolation problems. The ECH typically has to undergo various purification steps before it can be used for subsequent reactions.

For instance, the process for the manufacture of ECH in WO2004/048353 is carried out in a reaction medium comprising at least 75% w of organic material, causing significant isolation problems. Moreover, it is known from this reference and other references wherein ECH is made that the product of such processes frequently comprises both epichlorohydrin and the various byproducts resulting from the opening of the oxirane ring, namely 1-chloro-3-methoxy-2-propanol, 1-chloro-2-methoxy-3-propanol, 3-chloro-1,3-propanediol and 1,3-dichloro-2-propanol.

From the above it is clear the industry is still looking for a commercially feasible process for the manufacture of ECH, in high turnover numbers and at high selectivity, meaning free of byproducts such as diols. This process should also allow the use of an aqueous solvent as reaction medium, to avoid environmental and other problems related to acetonitrile and similar organic solvents. The present invention overcomes these disadvantages.

DISCLOSURE OF THE INVENTION

Accordingly, the invention provides a process for the manufacture of epichlorohydrin ("ECH") by catalytic oxidation of allyl chloride ("AC") with an oxidant wherein the catalytic oxidation is performed in an aqueous reaction medium, wherein a water-soluble manganese complex is used as oxidation catalyst, followed by the isolation of epichlorohydrin.

In a preferred embodiment, the ECH or part of the ECH is isolated as an organic phase, which phase comprises ECH or a mixture of allyl chloride and ECH. Moreover, there may be two organic phases with differing amounts of AC and ECH and hence different densities.

MODE(S) FOR CARRYING THE INVENTION

As used in the current specification, the expressions epoxidation and oxidation refer to the same reaction; the conversion of the carbon-carbon double bond of the allyl chloride into an oxirane ring. The invention is hereafter discussed in greater detail.

It is rather surprising that the current process can be used to prepare ECH at high selectivity with no noticeable amounts of byproducts (diols and such), despite having the reaction performed in an aqueous reaction medium.

In terms of water-soluble manganese complexes that may be used as oxidation catalyst, many suitable complexes are known. Note in this respect that what is described in this patent is actually the catalyst precursor. Indeed, in all open and patent literature typically a catalyst precursor is defined, as the active species during the system may be different and in fact even changing during the reaction that it catalyses. For convenience sake, and as this is common in the literature, we refer to the complex as if it is the catalyst.

Typically the catalyst comprises a manganese atom or a number of manganese atoms coordinated with a ligand or ligands. The manganese atom(s) may be in a II, III or IV oxidation state and be activated during the reaction. Of particular interest are binuclear Manganese complexes. Suitable manganese complexes therefore include mononuclear species of the general formula (I):

$$[LMnX_3]Y \qquad (I)$$

and binuclear species of the general formula (II):

$$[LMn(\mu\text{-}X)_3MnL]Y_2 \qquad (II)$$

wherein Mn is a manganese; L or each L independently is a polydentate ligand, preferably a cyclic or acyclic compound containing 3 nitrogen atoms; each X independently is a coordinating species and each μ-X independently is a bridging coordinating species, selected from the group consisting of: RO⁻, Cl⁻, Br⁻, I⁻, F⁻, NCS⁻, N₃⁻, I₃⁻, NH₃, NR₃, RCOO⁻, RSO₃⁻, RSO₄⁻, OH⁻, O²⁻, O₂²⁻, HOO⁻, H₂O, SH⁻, CN⁻, OCN⁻, and S₄²⁻ and combinations thereof, wherein R is a $C_1$-$C_{20}$ radical selected from the group consisting of alkyl, cycloalkyl, aryl, benzyl and combinations thereof, and Y is an oxidatively-stable counterion. Counterion Y may for instance be an anion selected from the group consisting of RO⁻, Cl⁻, Br⁻, I⁻, F⁻, SO₄²⁻, RCOO⁻, PF₆⁻, acetate, tosylate, triflate (CF₃SO₃⁻) and a combination thereof with R once again being a $C_1$ to $C_{20}$ radical selected from the group consisting of alkyl, cycloalkyl, aryl, benzyl and combination thereof. The type of anion is not very critical, although some anions are more preferred than others. A preferred counterion is PF₆⁻. Ligands which are suitable for the present invention are acyclic compounds containing at least 7 atoms in the backbone or cyclic compounds containing at least 9 atoms in the ring, each having the nitrogen atoms separated by at least two carbon atoms. A preferred class of ligands is that based on (substituted) triazacyclononane ("Tacn"). The prefer ligand is 1,4,7-trimethyl-1,4,7,-triazacyclononane ("TmTacn"), which is commercially available from for instance Aldrich. In this respect it is important to note that the water-solubility of the manganese catalyst is a function of all the aforementioned catalyst components. For instance, a mononuclear manganese complex prepared from $MnSO_4$ and TmTacn was found to be insufficiently soluble.

Dinuclear manganese complexes are preferred, because of their greater activity and solubility in water. Preferred dinuclear manganese complexes are those of the formula $[Mn^{IV}_2(\mu\text{-}O)_3L_2]Y_2$, wherein L and Y have the meaning identified above, preferably TmTacn as ligand, and $PF_6^-$ as counterion.

According to the present invention, the manganese complex may be utilized directly or as adsorbed onto a solvent insoluble support surface. Illustrative but nonlimiting examples of such substrates are structured aluminosilicates (e.g. Zeolite A, faujasite and sodalite), amorphous aluminosilicates, silica, alumina, charcoal, microporous polymeric resins (e.g. polystyrene beads formed through high internal phase emulsion technology) and clays (especially layered clays such as hectorite and hydrotalcite). Relative weight ratios of the manganese complex to the support may range anywhere from about 10:1 to about 1:10,000.

The manganese complex is used in catalytically effective amounts. Typically, the catalyst is used in a molar ratio of catalyst (Mn) versus allyl chloride of from 1:10 to 1:10,000,000, preferably of from 1:20 to 1:100,000, most preferably of from 1:50 to 1:1000. As a matter of convenience the amount of catalyst may also be expressed in terms of its concentration, when keeping in mind the volume of the aqueous medium. For instance, it may be used in a molar concentration (based on the Mn) of from 0.001 to 10 mmol, preferred of from 0.01 to 7 mmol and most preferably of from 0.01 to 2 mmol. In this respect it is also important to note that the epoxidation is first order on the catalyst concentration and proportional to the catalyst amount. With increase in the catalyst amount, the activity increases. The higher amounts, however, need to be balanced by the higher cost.

An advantage of the current invention, using a water soluble manganese complex is that the catalyst essentially does not migrate to the organic phase.

The aqueous reaction medium typically is a water phase containing AC and/or ECH and less than 25% by volume, preferably only minor amounts, if any, of other organic compounds. Although not preferred, the reaction medium may contain minor amounts of co-solvents such as methanol and acetone and the like. Whilst excluding the presence of AC and/or ECH, the aqueous reaction medium therefore suitably comprises at least 90% by volume of water, preferably 95% v, more preferably 99% v, still more preferably 99.9% v of water. Most preferably, however, the aqueous reaction medium (again, excluding any AC and/or ECH dissolved therein) is essentially a 100% water phase.

The aqueous reaction medium may contain a buffer system so as to stabilize the pH. For instance, it has been found that the aqueous reaction medium is suitably stabilized in a pH range of 2.5 to 8, whereas the preferred pH range is between 3 and 7 and the most preferred is between 3.5 to 6.5. The pH is therefore (well) below that used when bleaching olefins, typically carried out at more alkaline conditions (e.g., pH adjusted with $NaHCO_3$ to 9.0). The suitable or preferred range may be achieved by several known acid-salt combinations, with the preferred combination being based on oxalic acid-oxalate salt, or acetate acid-acetate salt. When oxalic acid and sodium oxalate are used, the pH ratio may be varied from 3.7 to 4.2. Typically, this buffer may be used in a molar ratio to the catalyst of about 10:1, but the amounts may be varied broadly, e.g., ranging from 1:1 to 100:1.

The aqueous reaction medium may also contain a phase transfer agent and/or a surfactant. Known phase transfer agents that may be used in the process of the invention include quaternary alkyl ammonium salts. Known surfactants that may be used in the process of the invention include non ionic surfactants such as Triton X100™ available from Union Carbide.

It is believed to be beneficial that the aqueous reaction medium contains at least trace amounts of allyl chloride. Although this is purely a hypothesis, it is believed that the presence of allyl chloride allows the catalyst to remain active, whereas it is believed that without the presence of allyl chloride and/or due to the presence of ECH and/or oxidant without allyl chloride present the activity of the active catalyst reduces.

The reaction conditions for the catalytic oxidation may be quickly determined by a person skilled in the art. Pressure is not of particular relevance. The reaction is believed to be exothermic, and cooling of the reaction medium may be required. The reaction is preferably carried out at temperatures anywhere from −5° C. to 30° C., preferably from 0° C. to 20° C., and most preferably from 0° C. to 10° C.

It is noted that the reaction product ECH, is present in very small amounts in the aqueous phase. Instead, ECH forms an organic phase, together with the (surplus of) allyl chloride, if present. Of particular interest in the process of the current invention is that the reaction product, ECH, can form a separate phase. Thus, by proper selection of the reaction conditions, catalytically effective amount of a water-soluble manganese complex as epoxidation catalyst and an aqueous reaction medium, it has been found that allyl chloride is converted into ECH which then separates from the aqueous reaction medium due to its limited solubility, forming a product layer or product layers comprising ECH that is/are free of any byproducts and free of any organic solvents. The ECH product layer may contain some unreacted allyl chloride dissolved therein. As a matter of fact, there may be two product layers, differing in concentration of allyl chloride and ECH which therefore may have a density greater or smaller than the density of the aqueous reaction medium.

To achieve the high selectivity and turnover numbers of the current invention, the allyl chloride and oxidant are preferably reacted at a molar ratio of from 1:0.1 to 1:10, more preferably of from 1:0.2 to 1:1.2, still more preferably of from 1:0.8 to 1:1. Allyl chloride is preferably used in equimolar excess of oxidant. The amount of reactants should be such that at full conversion of the allyl chloride more ECH is produced than is soluble in the aqueous reaction medium. Preferably, the amount of reactants is such at that 80% conversion of the allyl chloride more ECH is produced than is soluble in the aqueous reaction medium. More preferably, the amount of reactants is such at that 50% conversion of the allyl chloride more ECH is produced than is soluble in the aqueous reaction medium. This process results in the production of ECH at high turnover numbers, with high selectivity towards ECH with moreover improved ease of isolating the ECH. To ensure optimal results, the addition of reactants should be to the aqueous medium and not to the organic phase, should that have formed during the reaction.

As mentioned before, it is believed beneficial to have some allyl chloride present in the aqueous reaction medium. Mixing an organic phase, if present, rich in allyl chloride with the aqueous phase may be beneficial, whereas back-mixing an organic phase purely composed of ECH should preferably be avoided. Thus, it is believed that mixing or stirring improves the conversion of allyl chloride into ECH, but that ECH itself retards the conversion of allyl chloride.

The conversion of allyl chloride ("AC") into epichlorohydrin is discussed hereinafter. Depending on the reaction conditions, the reaction may be performed in a three layer system comprising an organic phase at the bottom, and an organic phase on top. The phase at the bottom may have a higher density then the reaction medium, for instance caused by a relatively high ECH content, whereas the organic phase on top will have lower density then the reaction medium, for instance caused by a relatively high AC content. Subject to a.o. the stirring conditions, however, it may not be immediately apparent that such separate phases exist or are being created during the reaction; for instance the separate phase(s) may be observed only after the system has been in rest. The catalytic oxidation of the present invention is carried out preferably using hydrogen peroxide as oxidant. Other oxidants may be used, i.e. as precursor to the hydrogen peroxide, but given the availability and to reduce environmental impact hydrogen peroxide is the preferred oxidant. Hydrogen peroxide has strong oxidizing properties. As bleaching agent it is mostly used for bleaching paper. It is typically used in an aqueous solution. The concentration of hydrogen peroxide may vary, from 15% (e.g., consumer grade for bleaching hair) to 98% (propellant grade), with a preference for industrial grades varying from 20 to 60%, preferably from 30 to 50%.

To ensure optimal oxidant efficiency, the oxidant is preferably added to the aqueous reaction medium at a rate about equal to the reaction rate of the catalytic oxidation.

The catalytic oxidation may be performed in a batch process, in a continuous process or in a semi-continuous process. Indeed, the process may be modified in various aspects without departing from the gist of the invention.

By way of general example the catalytic oxidation of allyl chloride is described hereafter.

The catalytic oxidation may be performed in a common stirred tank reactor provided with a means of stirring. For instance, this may be a common blade agitator operating under an agitation speed of around 250 rpm. The catalyst, aqueous reaction medium and reactants may be added in batch, or the reactants may be added over a period of time. If hydrogen peroxide is added during the reaction, then it is added to either the (stirred) organic phase comprising the allyl chloride or the (stirred) aqueous reaction medium.

In (semi)continuous operations, various recycling streams may be used to control the reaction conditions (maintained at a temperature of between −5° C. and 10° C.) and to optimize the production rate.

In terms of process design, a settler may be added to optimize the gravitational separation of the ECH. Likewise, a membrane unit may be used to recycle the aqueous reaction medium with reduced loss of catalyst.

On example of a mass balance for the reaction process according to the invention is:

| | |
|---|---|
| ECH | about 11 000 kg/h |
| AC | about 9 100 kg/h |
| $H_2O_2$(35%) | about 6 457 kg/h |
| $H_2O$ | about 2 140 kg/h |

As a result of this mass balance, the ratio ECH/cat is about 8000 mol/mol.

The following examples will more fully illustrate selected embodiments of this invention. All parts, percentages and proportions referred to herein and in the appended claims are by weight unless otherwise indicated.

EXAMPLES

Example 1

The catalytic oxidation was carried out with a catalyst of the formula:

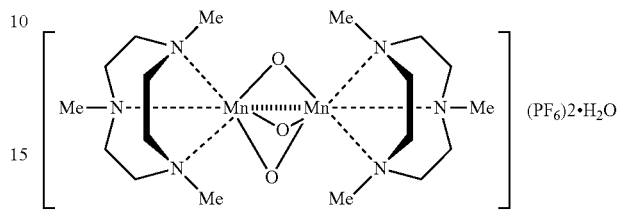

Also used is an oxalate/oxalic acid buffer, with 35% aqueous $H_2O_2$ as oxidant, and water as aqueous reaction medium. The experiment is carried out with allyl chloride as the terminal olefin.

Experimental

In a typical epoxidation reaction 9.3 µmol of catalyst in 50 mL of water, 112.5 µmol of sodium oxalate in 7.5 mL of $H_2O$ and 112.5 µmol of oxalic acid in 7.5 mL of $H_2O$ were taken into a three-neck round-bottomed flask equipped with a mechanical stirrer. The reaction started with the addition of olefin (150 mmol) and dilute $H_2O_2$ (200 mmol) at 4° C.

10 mL of extra water was added as solvent for the reaction. The oxidant was added under flow conditions with 8.8 mL/hr into the reaction solution. The pH of the reaction solution was 3.5 to 3.6 and the stirring rate was maintained at 210 rpm for the most of the experiments with mechanical stirrer.

Results and Discussion

The manganese complex produced ECH efficiently using water as solvent. During the epoxidation using water as solvent, at the beginning of the reaction, AC was present as a separate layer on top of the aqueous catalyst solution. As the epoxidation progressed the ECH was formed in a separate phase along with some AC dissolved in it. The reaction was performed several times. On occasion the system formed three phases from top to bottom: an organic, an aqueous and a second organic phase. At the end of the reaction both the top and bottom organic phases comprised major amounts of ECH and AC. Minor amounts of AC and ECH were also found in the aqueous phase. On the other hand, the system has also resulted in a two layer system, with an organic phase (comprising AC and ECH), and an aqueous phase.

This example provided a 50% yield of ECH based on allyl chloride, produced at 40% selectivity of hydrogen peroxide, with 7800 TON. There were no noticeable amounts of diols or other side products produced.

Example 2

Various experiments were carried out in the manner of Example 1. In Table 1 the results of the epoxidation of AC at various stirring rates are presented.

TABLE 1

Epoxidation of AC: Variation of stirring rate

| No. | Time period (h) | Stirring rate (rpm) | ECH (mmol) | TON (for ECH) |
|---|---|---|---|---|
| 1 | 6 | 650 | 33 | 3500 |
| 2 | 6 | 500 | 36 | 3900 |
| 3 | 6 | 210 | 73 | 7800 |
| 4 | 4 | 210 | 64 | 6900 |
| 5 | 4 | 100 | 37 | 3900 |

This example illustrates that the yield of ECH increases with the stirring rate until an optimum has been reached.

Example 3

Variation in Catalyst Amount

The rate of the production of ECH was proportional to the concentration of the catalyst. This example illustrates that increased amounts of catalyst leads to increased production of ECH.

TABLE 2

Epoxidation of AC: Variation of catalyst amount

| No. | Time period (h) | Catalyst amount (μmol) | Efficiency peroxide (%) | ECH (mmol) | TON |
|---|---|---|---|---|---|
| 1 | 4 | 4.7 | 30 | 30 | 6400 |
| 2 | 4 | 9.4 | 42 | 64 | 6900 |
| 3 | 4 | 18.3 | 46 | 66 | 3600 |

Example 4

Effect of pH

In the previous experiments the epoxidation reactions have been performed at low pH around 3.5 to 3.6. Here we show that the catalyst was active in both acidic and basic conditions, that is at pH=2.6 with only oxalic acid present, as well as at pH=8 with only sodium oxalate. These results give evidence that the catalyst system was active in the wide pH range for AC epoxidation.

TABLE 2

Effect pH for epoxidation of allyl chloride

| | | peroxide | mmol of ECH formed | | | |
|---|---|---|---|---|---|---|
| No. | pH | consumed (mmol) | in Organic phase | in Aqueous phase | TON ECH | Selectivity of peroxide (%) |
| 1 | 2.6 | 55 | 15.4 | 7.6 | 2400 | 42 |
| 2 | 8 | 121 | 29 | 19 | 5000 | 39 |

The invention claimed is:

1. A process for the manufacture of epichlorohydrin, comprising:
reacting allyl chloride with an hydrogen peroxide in the presence of a catalyst in an aqueous reaction medium in a system having one or two organic phases, wherein the catalyst comprises a water-soluble manganese complex and the molar ratio of allyl chloride to hydrogen peroxide is from 1:0.1 to 1:1; and
isolating an epichlorohydrin product in the one or two organic phases, and wherein the water-soluble manganese complex is selected from a mononuclear manganese complex of the formula (I):

[LMnX$_3$]Y        (I)

or a binuclear manganese complex of the formula (II):

[LMn(μ-X)$_3$MnL]Y$_2$        (II)

wherein Mn is a manganese atom; L or each L independently is a polydentate ligand of triazacyclononane or a substituted triazacyclononane; each X independently is a coordinating species selected from the group consisting of: RO$^-$, Cl$^-$, Br$^-$, I$^-$, F$^-$, NCS$^-$, N$_3$$^-$, I$_3$$^-$, NH$_3$, NR$_3$, RCOO$^-$, RSO$_3$$^-$, RSO$_4$$^-$, OH$^-$, O$^{2-}$, O$_2$$^{2-}$, HOO$^-$, H$_2$O, SH$^-$, CN$^-$, OCN$^-$, and S$_4$$^{2-}$ and combinations thereof, wherein R is a C$_1$-C$_{20}$ radical selected from the group consisting of alkyl, cycloalkyl, aryl, benzyl and combinations thereof and each μ-X independently is a bridging coordinating species selected from the group consisting of: RO$^-$, Cl$^-$, Br$^-$, I$^-$, F$^-$, NCS$^-$, N$_3$$^-$, I$_3$$^-$, NH$_3$, NR$_3$, RCOO$^-$, RSO$_3$$^-$, RSO$_4$$^-$, OH$^-$, O$^{2-}$, O$_2$$^{2-}$, HOO$^-$, H$_2$O, SH$^-$, CN$^-$, OCN$^-$, and S$_4$$^{2-}$ and combinations thereof, wherein R is a C$_1$-C$_{20}$ radical selected from the group consisting of alkyl, cycloalkyl, aryl, benzyl and combinations thereof, and Y is an anion counterion selected from the group consisting of RO$^-$, Cl$^-$, Br$^-$, I$^-$, F$^-$, SO$_4$$^{2-}$, RCOO$^-$, PF$_6$$^-$, acetate, tosylate, triflate (CF$_3$SO$_3$$^-$) and a combination thereof, wherein R is a C$_1$-C$_{20}$ radical selected from the group consisting of alkyl, cycloalkyl, aryl, benzyl and combinations thereof, wherein the aqueous reaction medium further comprises a buffer system so as to stabilize the pH and a pH in the range of from 3 to 6.5.

2. The process of claim 1, wherein the one or two organic phases comprise epichlorohydrin product or a mixture of allyl chloride and epichlorohydrin product.

3. The process of claim 1, wherein the manganese complex comprises the formula [LMn(μ-X)$_3$MnL]Y$_2$, wherein Mn is a manganese atom; L is a L is a triazacyclononane or substituted triazacyclononane; each X independently is a coordinating species: and each μ-X independently is a bridging coordinating species, selected from the group consisting of: RO$^-$, Cl$^-$, Br$^-$, F$^-$, NCS$^-$, N$_3$$^-$, I$_3$$^-$, NH$_3$, NR$_3$, RCOO$^-$, RSO$_3$$^-$, RSO$_4$$^-$, OH$^-$, O$^{2-}$, HOO$^-$, H$_2$O, SH$^-$, CN$^-$, OCN$^-$, and S4$^{2-}$ and combinations thereof, wherein R is a C$_1$-C$_{20}$ radical selected from the group consisting of alkyl, cycloalkyl, aryl, benzyl and combinations thereof, and Y is SO$_4$$^{2-}$, PF$_6$$^-$, acetate, or a combination thereof.

4. The process of claim 1, further comprising agitating the aqueous reaction medium and the one or two organic phases.

5. The process of claim 4, wherein the stirring the aqueous reaction medium comprises stirring the system with a stirrer at between 100 rpms and 650 rpm.

6. The process of claim 1, wherein the aqueous reaction medium further comprises a buffer system at a buffer to catalyst ratio from 10:1 to 100:1.

7. The process of claim 6, wherein the buffer system comprises an acid-salt combination.

8. The process of claim 7, wherein the acid-salt combination comprises oxalic acid-oxalate salt or acetic acid-acetate salt.

9. The process of claim 1, wherein the catalyst is present in a concentration from 0.001 mmol/L to 10 mmol/L.

10. The process of claim 1, wherein the catalyst is used in a molar ratio of the catalyst (Mn) to the allyl chloride from 1:10 to 1:10,000,000.

11. The process of claim 1, wherein the aqueous reaction comprises a pH in the range of from 3 to 6.5.

12. The process of claim 1, wherein the aqueous reaction comprises a pH in the range of from 3 to 4.2.

13. The process of claim 1, wherein the allyl chloride and the hydrogen peroxide are reacted at a molar ratio of the allyl chloride to the hydrogen peroxide in the range from 1:0.2 to 1:0.8.

14. The process of claim 1, wherein the reaction is performed in a batch process, in a continuous process or in a semi-continuous process.

15. The process of claim 1, wherein the aqueous reaction medium comprises a 100% aqueous medium excluding any dissolved epoxide and allyl chloride.

16. The process of claim 1, wherein the manganese complex comprises the formula [LMn(μ-X)$_3$MnL]Y$_2$, wherein L is a triazacyclononane or substituted triazacyclononane and the counterion Y is PF$_6^-$ or CH$_3$CO$_2^-$.

17. The process of claim 1, wherein the catalyst comprises a binuclear manganese complex of the general formula (II):

$$[LMn(\mu\text{-}X)_3MnL]Y_2 \qquad (II),$$

wherein Mn is a manganese; L or each L independently is a polydentate ligand of triazacyclononane or a substituted triazacyclononane; each μ-X independently is a bridging coordinating species of: O$^{2-}$, RCOO$^-$, RSO$_3^-$, RSO$_4^-$, wherein R is selected from the group consisting of C$_1$-C$_{20}$ alkyl, C$_1$-C$_{20}$ cycloalkyl, C$_1$-C$_{20}$ aryl, benzyl and combinations thereof, and Y is an anion selected from the group consisting of SO$_4^{2-}$, PF$_6^-$, acetate, and a combination thereof;

wherein the aqueous reaction medium further comprises a buffer system with a pH range from 3 to 4.2; and wherein the molar ratio of the terminal olefin to the hydrogen peroxide in the range of from 1:0.1 to 1.2:1.

* * * * *